United States Patent
Pfaff et al.

(12)

(10) Patent No.: US 6,267,810 B1
(45) Date of Patent: Jul. 31, 2001

(54) PIGMENT MIXTURE

(75) Inventors: Gerhard Pfaff, Munster; Sabine Schoen, Darmstadt, both of (DE); Nishimagi Atsuko, Fukushima-pref. (JP)

(73) Assignee: Merck Patent Gesellschaft mit beschraenkter Haftung (DE)

( * ) Notice: Subject to any disclaimer, the term of this patent is extended or adjusted under 35 U.S.C. 154(b) by 0 days.

(21) Appl. No.: 09/471,330

(22) Filed: Dec. 23, 1999

(30) Foreign Application Priority Data

Dec. 23, 1998 (EP) .................................. 98124473

(51) Int. Cl.$^7$ ............................... C09C 1/00; C09C 1/04; C09C 1/24; C09C 1/36; C09C 1/40
(52) U.S. Cl. .......................... 106/415; 106/404; 106/417; 106/426; 106/442; 106/483
(58) Field of Search .................................... 106/404, 415, 106/417, 426, 442, 483

(56) References Cited

U.S. PATENT DOCUMENTS

| 5,749,946 | * | 5/1998 | Glausch et al. ............... 106/14.17 |
| 6,113,683 | * | 9/2000 | Herren et al. ..................... 106/494 |
| 6,139,962 | * | 10/2000 | Herget et al. ...................... 428/404 |

\* cited by examiner

*Primary Examiner*—Mark L Bell
*Assistant Examiner*—Michael J. DiVerdi
(74) *Attorney, Agent, or Firm*—Millen, White, Zelano, & Branigan, P.C.

(57) ABSTRACT

The present invention relates to pigment mixtures containing at least two components, component A being $Al_2O_3$ flakes coated with one or more metals, metal oxides and/or metal sulfides and component B being special-effect pigments, and to their use in varnishes, paints, printing inks, masterbatches, plastics and cosmetic formulations.

16 Claims, No Drawings

PIGMENT MIXTURE

SUMMARY OF THE INVENTION

The present invention relates to pigment mixtures containing at least two components, component A being $Al_2O_3$ flakes coated with one or more metals, metal oxides and/or metal sulfides and component B being special-effect pigments, and to their use in varnishes, paints, printing inks, plastics and cosmetic formulations.

With platelet-shaped pigments, hiding power and gloss are often difficult to realise simultaneously to a satisfactory extent. For instance, $SiO_2$ flakes or mica platelets covered with one or more thin metal oxide layers feature interference colors and a high luster but at the same time, owing to the transparent substrate, feature high transparency and hence a comparatively poor hiding power.

Thus EP 0 562 329 discloses a pigment mixture comprising iron oxide-coated $SiO_2$ flakes in combination with iron oxide-coated mica pigments.

DE-A-42 40 511 discloses a pigment mixture which consists of an interference pigment and a platelet-shaped color pigment. The interference pigment comprises metal oxide-coated mica flakes or $SiO_2$ flakes, and the color pigment can be colored, uncoated $SiO_2$ flakes. This pigment mixture is incorporated into coating materials, printing inks or plastics.

The object of the present invention is to provide a pigment mixture which is notable for relatively high hiding power and which lends itself well to incorporation into the respective system in which it is used, and for which at the same time a separation of pigment/colorant in the system is largely ruled out.

Surprisingly, pigment mixture has now been found which has none of the disadvantages indicated above. The pigment mixture of the invention consists of at least two components, component A being $Al_2O_3$ flakes coated with one or more metals, metal oxides and/or metal sulfides and component B being one or more special-effect pigments. The admixture of the special-effect pigments with the coated $Al_2O_3$ flakes is able to give the systems in which they are used a multiple flop, the color effect is intensified, and new color effects are achieved.

The invention thus provides a pigment mixture containing at least two components, component A and component B. Component A comprises $Al_2O_3$ flakes coated with one or more metals, metal oxides and/or metal sulfides. The $Al_2O_3$ flakes comprise platelet-shaped $Al_2O_3$ substrates. Component B comprises one or more special-effect pigments.

The invention likewise provides the formulations, such as paints, varnishes, printing inks, plastics, agricultural films and cosmetic formulations, which comprise the pigment mixture of the invention.

The coated $Al_2O_3$ flakes can be mixed in any proportion with the special-effect pigments. The ratio of component A to component B is preferably from 1:10 to 10:1, in particular from 3:1 to 5:1.

Coated aluminum oxide in a flaky form is commercially available, for example, from Merck KGaA under the tradename Xirallic®.

α-$Al_2O_3$ in the form of hexagonal flakes having a particle diameter greater than 10 μm and an aspect ratio (particle diameter/thickness) of 5–10 is known from JP 111239/1982 (Laid Open No.).

The Japanese Patent Publication No. 72527/1991 disclose α-$Al_2O_3$ in the form of flakes having an average particle diameter of 0.5–3 μm.

The JP 39362/1992 (Laid Open No.) describes $Al_2O_3$ in the form of fine platy particles of a hexagonal crystal system with the plane perpendicular to the c axis grown into a plate.

Preferred $Al_2O_3$ flakes are flakes composed of aluminum oxide (as a major consituent) and of titanium dioxide (as minor consituent) which are known from U.S. Pat. No. 5,702,519. These $Al_2O_3$ flakes are prepared from a uniform aqueous solution of water-soluble aluminum salt and titanium salt by hydrolysis with an alkali carbonate aqueous solution in the presence of an aqueous solution containing an alkali metal salt like alkali metal sulfate and phosphoric acid or phosphate, drying by evaporation (dehydration by heating), and molten salt treatment.

The $Al_2O_3$ flakes are provided with one or more metal oxide layers. Examples of suitable metal oxides or metal oxide mixtures are titanium dioxide, zirconium oxide, zinc oxide, iron oxides ($Fe_2O_3$ and/or $Fe_3O_4$) and/or chromium oxide, especially $TiO_2$ and/or $Fe_2O_3$. The $Al_2O_3$ flakes can be coated in the same way as pearl luster pigments. Coatings with a metal oxide may be accomplished by any known methods, such as hydrolysis of a metal salt by heating or alkali, which deposits hydrated metal oxide, followed by calcination.

$Al_2O_3$ flakes can also be coated with one or more layers of a metal or metal alloy selected, for example, from chromium, nickel, silver, bismuth, copper, tin, or hastalloy. $Al_2O_3$ flakes coated with a metal sulfide are coated with, for example, sulfides of tungsten, molybdenum, cerium, lanthanum or rare earth elements.

The $Al_2O_3$ flakes can be coated by wet chemical coating, by CVD or PVD processes. The metal coating on the $Al_2O_3$ flakes functions to increase the hiding power of the pigment.

Suitable components B for the pigment mixture of the invention are all special-effect pigments familiar to the skilled worker in the effect pigment sector, examples being metal effect pigments, such as aluminum, copper, zinc, tin and their alloys. Aluminum and gold bronze alloys are preferably to be mentioned, especially those having a particle size of 2 to 40 μm.

The pigment mixtures of the invention preferably comprise uncoated and coated platelet-shaped iron oxide, aluminum flakes or coated aluminum flakes. Special-effect pigments of this kind are marketed by BASF under the name Paliocrom®, by Eckart-Werke under the name Stapa®, and by the Flex Company under the name ChromaFlair®. The following pigments should also be mentioned: Pearl luster pigments, $TiO_2$ flakes or $SiO_2$ flakes coated with one or more metal oxides, such as $TiO_2$ or $Fe_2O_3$, for example, graphite platelets, ceramic platelets BiOCl or glass flakes coated with one or more metal oxides, liquid crystal polymer particles (LCP), holographic pigments and multilayer pigments.

Pearl luster pigments, mica flake pigments coated with one or more metal oxides, are obtainable, for example, from Merck KGaA, Darmstadt, under the tradenames Iriodin®, Afflair® and Timiron®. The latter pigments are known, for example, from the German Patents and Patent Applications 14 67 468, 19 59 998, 20 09 566, 22 14 545, 22 15 191, 22 44 298, 23 13 331, 25 22 572, 31 37 808, 31 37 809, 31 51 343, 31 51 354, 31 51 355, 32 11 602 and 32 53 017. Mica pigments coated with $TiO_2$ and/or $Fe_2O_3$ are employed in particular. As phyllosilicates, both natural and synthetic mica are suitable.

Additionally, the inventive pigment mixture can contain organic or inorganic colorants, thixotropic agents, wetting agents, dispersing agents, water, organic solvent or solvent mixtures, etc.

The pigment mixture of the invention is simple and easy to handle. The pigment mixture can be incorporated into the system in which it is used by simple stirring. Laborious milling and dispersing of the pigments is not necessary.

The pigment mixture of the invention can be used for pigmenting coating materials, printing inks, plastics, agricultural films, button pastes, for the coating of seed, for the coloring of food, coatings of medicaments or cosmetic formulations. The concentration of the pigment mixture in the system in which it is to be used for pigmenting is generally between 0.01 and 50% by weight, preferably between 0.1 and 5% by weight, based on the overall solids content of the system. This concentration is generally dependent on the specific application.

Plastics comprising the pigment mixture of the invention in amounts of 0.1 to 50% by weight, in particular from 0.5 to 7% by weight, are frequently notable for a particular sparkle effect.

In the coating sector, especially in automotive finishing, the pigment mixture is employed in amounts of 0.5–10% by weight. The proportion in which the coated $Al_2O_3$ flakes are mixed with component B, especially coated $SiO_2$ flakes or coated mica platelets, depends on the desired effect. The $Al_2O_3$ flakes are preferably employed with component B in a ratio of 1:10 to 10:1, in particular of 3:1.

In the coating material, the pigment mixture of the invention has the advantage that the desired color flop effect is obtained by a single-layer coating (one-coat systems or as a base coat in a two-coat system). This color flop is extremely pronounced even under diffuse light. In comparison with coatings which comprise an interference pigment rather than the coated $Al_2O_3$ flakes, coatings with the pigment mixture of the invention exhibit a marked depth effect and a glitter effect and also a strong color flop.

In the pigmentation of binder systems, for example for paints and printing inks for intaglio, offset printing or screen printing, pigment mixtures consisting of coated $Al_2O_3$ flakes with Stapa®-aluminum and gold bronze pastes from Eckart-Werke have proven particularly suitable. The pigment mixture is incorporated into the printing ink in amounts of 2–50% by weight, preferably 5–30% by weight and, in particular 8–15% by weight. The mixing ratio of component A to component B is preferably in the range from 1:10 to 10:1. The printing inks comprising the pigment mixture of the invention exhibit purer hues and are of improved printability owing to the good viscosity values.

The invention likewise provides pigment preparations comprising coated $Al_2O_3$ flakes, effect pigments, binders and, if desired, additives, the said preparations being in the form of substantially solvent-free, free-flowing granules. Such granules contain up to 95% by weight of the pigment mixture. A pigment preparation in which the pigment mixture of the invention is pasted up with a binder and with water and/or an organic solvent, with or without additives, and the paste is subsequently dried and brought into a compact particulate form, e.g., granules, pellets, briquettes, a masterbatch or tablets, is particularly suitable as a precursor for printing inks.

The present invention therefore also provides formulations containing the pigment mixture of the invention.

In the foregoing and in the following examples, all temperatures are set forth uncorrected in degrees Celsius; and, unless otherwise indicated, all parts and percentages are by weight.

The entire disclosure of all applications, patents and publications, cited herein are hereby incorporated by reference. Particularly, this application claims priority to European Patent Application 98124473.4, the entire text of which is hereby incorporated by reference. Additionally, U.S. patent applications having application Ser. Nos. 09/471,331, 09/471,269, and 09/471,004 are hereby incorporated by reference.

EXAMPLES

Example 1

Paint

| | Formulations consisting of |
|---|---|
| 2.50% | $Fe_2O_3$-coated $Al_2O_3$ flakes having a particle size of 5–60 μm (Merck KGaA) |
| 1.50% | Monastral green 6Y spec. (Zeneca) |
| 0.50% | Cappoxyt yellow 4214 (Capelle) |
| 0.03% | Pigment-grade carbon black FW 200 (Degussa) |
| 0.40% | Dollaraluminum Alpate 7620 NS (Alcan Toyo Europe) |

Remainder: Paint base with 19% solids content (acrylate-melamine) and diluent mixture

Example 2

Intaglio Printing

| Printing ink consisting of |
|---|
| 70 g nitrocellulose-based binder from Gebrüder Schmidt, 95MB011, with solids content of about 20% |
| 30 g pigment, i.e. 15 g of Cromal IV (Eckart) AL 14–18 μm and 15 g of $Fe_2O_3$-coated $Al_2O_3$ flakes of particle size 5–60 μm |
| 30 g 1-ethoxy-2-propanol |

Example 3

Plastic 1 kg of polystyrene granules are wetted uniformly in a tumble mixer with 5 g of adhesion agent. Then 35 g of $Fe_2O_3$-coated $Al_2O_3$ flakes of particle size 5–60 μm and 7 g of Iriodin®121 (TiO$_2$-coated mica pigment from Merck KGaA, Darmstadt, FRG with particle size 5–20 μm) are added, and the components are mixed for 2 minutes.

These granules are processed under customary conditions on an injection moulding machine to give small stepped plates measuring 4×3×0.5 cm. The small stepped plates are notable for their luster.

Example 4

Eye Shadow

| Phase A | |
|---|---|
| 15.00% | $TiO_2$-coated $AL_2O_3$ flakes of particle size 5–60 μm (Merck KGaA) |
| 15.00% | Timiron ® Super Blue ($TiO_2$-coated mica of particle size 10–60 Fm from (Merck KGaA) |
| 49.50% | Talc |

-continued

| | |
|---|---|
| 7.50% | Solanum Tuberosum (potato starch) |
| 2.50% | Magnesium stearate |
| Phase B | |
| 9.14% | Isopropyl stearate |
| 0.53% | Cetyl palmitate |
| 0.53% | Petrolatum |
| 0.21% | Fragrance |
| 0.11% | Preservative |

The constituents of Phase A are combined and formed into a premix. The melted phase B is then added dropwise with stirring to the powder mixture. The powders are pressed at 40–50 bar.

Example 5

Shower Gel

| | |
|---|---|
| Phase A | |
| 0.10% | $TiO_2$-coated $Al_2O_3$ flakes of particle size 5–60 μm (Merck KGaA) |
| 0.10% | Timiron ® Super Blue ($TiO_2$-coated mica of particle size 10–60 μm from Merck KGaA) |
| 0.75% | Xantham gum |
| ad 100.00% | Water |
| Phase B | |
| 20.00% | Decyl glycoside |
| 6.65% | Texapon ASV |
| | Sodium laureth sulfate |
| | Magnesium laureth sulfate |
| | Sodium laureth 8-sulfate |
| | Magnesium laureth 8-sulfate |
| | Sodium oleth sulfate |
| 0.20% | Preservative |
| 0.50% | Fragrance |
| Phase C | |
| 0.15% | Citric acid |
| 10.00% | Water |

For Phase A, the pigments are stirred into the water. The xanthan gum is scattered in slowly with stirring and the mixture is stirred until the gum has dissolved. Phases B and C are added in succession, and slow stirring is continued until all of the components are homogeneously distributed.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A pigment mixture comprising a component A and a component B, wherein component A comprises $Al_2O_3$ flakes coated with one or more metals, metal oxides or metal sulfides, and wherein component B comprises special-effect pigments.

2. A pigment mixture according to claim 1, wherein at least a portion of the $Al_2O_3$ flakes in component A comprise $Al_2O_3$ flakes coated with $TiO_2$, $Fe_2O_3$, or a mixture of $TiO_2$ and $Fe_2O_3$.

3. A pigment mixture according to claim 1, wherein component B comprises i) one or more of metal platelets coated with one or more metal oxides, ii) graphite platelets, iii) aluminum platelets, iv) phyllosilicates, v) $Fe_2O_3$-flakes, $SiO_2$-flakes, or $TiO_2$-flakes uncoated or coated with one or more metal oxides, vi) glass platelets and or vii) ceramic platelets.

4. A pigment mixture according to claim 2, wherein component B comprises i) one or more of metal platelets coated with one or more metal oxides, ii) graphite platelets, iii) aluminum platelets, iv) phyllosilicates, v) $Fe_2O_3$-flakes, $SiO_2$-flakes, or $TiO_2$-flakes uncoated or coated with one or more metal oxides, vi) glass platelets and or vii) ceramic platelets.

5. A pigment mixture according to claim 1, further comprising component A and component B in a ratio of 10:1 to 1:10.

6. A pigment mixture according to claim 2, further comprising component A and component B in a ratio of 10:1 to 1:10.

7. A pigment mixture according to claim 3, further comprising component A and component B in a ratio of 10:1 to 1:10.

8. A pigment mixture according to claim 4, further comprising component A and component B in a ratio of 10:1 to 1:10.

9. A method of manufacturing a pigment formulation comprising providing a pigment mixture according to claim 1 and adding the pigment mixture to formulation to obtain a paint, a varnish, a printing ink, a powder coating material, a master batch, a plastic, a formulation for coloring seed, a cosmetic formulation or a formulation for food enhancement.

10. A pigment formulation comprising a pigment mixture according to claim 1, wherein the pigment formulation is a paint, a varnish, a printing ink, a powder coating material, a master batch, a plastic, a formulation for coloring seed, a cosmetic formulation or a formulation for food enhancement.

11. A pigment formulation comprising a pigment mixture according to claim 2, wherein the pigment formulation is a paint, a varnish, a printing ink, a powder coating material, a master batch, a plastic, a formulation for coloring seed, a cosmetic formulation or a formulation for food enhancement.

12. A pigment formulation comprising of from 0.5% to 7% of a pigment mixture according to claim 1, wherein the pigment formulation is a plastic.

13. A pigment formulation comprising of from 0.5% to 10% of a pigment mixture according to claim 1, wherein the pigment formulation is an automotive finish.

14. A pigment formulation comprising of from 2.0% to 50% of a pigment mixture according to claim 1, wherein the pigment formulation is a printing ink.

15. A pigment preparation comprising a pigment mixture according to claim 1 and a binder, wherein the pigment preparation is substantially solvent free, and wherein the pigment preparation is substantially in the form of free flowing granules.

16. A pigment preparation comprising a pigment mixture according to claim 2 and a binder, wherein the pigment preparation is substantially solvent free, and wherein the pigment preparation is substantially in the form of free flowing granules.

* * * * *